United States Patent [19]
Gamblin et al.

[11] Patent Number: 5,795,846
[45] Date of Patent: Aug. 18, 1998

[54] HERBICIDAL COMPOSITIONS

[75] Inventors: Alan Gamblin; Richard Henry Hewett, both of Ongar, United Kingdom

[73] Assignee: Rhone-Poulenc Agriculture Limited, Ongar, United Kingdom

[21] Appl. No.: 881,381

[22] Filed: Jun. 24, 1997

Related U.S. Application Data

[63] Continuation of Ser. No. 508,556, Jul. 28, 1995, abandoned, which is a continuation of Ser. No. 283,756, Aug. 1, 1994, abandoned.

[60] Provisional application No. 60/000,019 Jun. 8, 1995.

[51] Int. Cl.⁶ ............................................ A01J 43/74
[52] U.S. Cl. ............................................. 504/128
[58] Field of Search ............................................. 504/138

[56] References Cited

U.S. PATENT DOCUMENTS

| | | | |
|---|---|---|---|
| 4,666,502 | 5/1987 | Seckinger et al. | 71/90 |
| 5,627,131 | 5/1997 | Shribbs et al. | 504/105 |

FOREIGN PATENT DOCUMENTS

| | | |
|---|---|---|
| 0 380447 | 8/1990 | European Pat. Off. . |
| 0 418 175 | 3/1991 | European Pat. Off. . |
| 0 487 357 | 5/1992 | European Pat. Off. . |
| 0 527 036 | 2/1993 | European Pat. Off. . |
| 0 560 482 | 9/1993 | European Pat. Off. . |

OTHER PUBLICATIONS

*The Pesticide Manual*, ninth edition, ed. Charles R. Worthing, The British Crop Protection Council, 1991, pp. 5, 13–14, 585 and 712–713.

Owen et al., *Res. Rep. North Cent. Weed Science Society*, vol. 46, p. 316 (1989).

*Chemical Abstracts*, vol. 120, No. 9, Feb. 28, 1994, abstract No. 99283.

*Primary Examiner*—Brian M. Burn
*Attorney, Agent, or Firm*—Connolly and Hutz

[57] ABSTRACT

The invention relates to herbicidal compositions comprising:

(a) a 4-benzoylisozaxole of formula I:

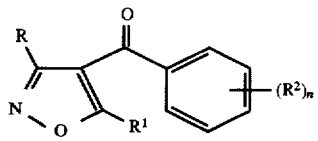

(I)

wherein R, $R^1$ and $R^2$ are as defined in the description and
(b) a chloroacetamide herbicide.

49 Claims, 8 Drawing Sheets

HERBICIDAL COMPOSITIONS

CROSS REFERENCE TO RELATED APPLICATION

This application is a continuation of U.S. patent application U.S. Ser. No. 08/508,556, (now abandoned) filed Jul. 28, 1995, which is is a continuation-in-part of prior U.S. patent application Ser. No. 08/283,756, filed Aug. 1, 1994, (now abandoned) and also claims the benefit of the filing date of prior United States Provisional Patent Application No. 60/000019, filed Jun. 8, 1995 (Attorney Docket No. 022650-315), said prior applications being incorporated by reference herein in their entireties and relied upon.

BACKGROUND OF THE INVENTION

This invention relates to new herbicidal compositions comprising a mixture of 4-benzoylisoxazoles and herbicidal chloroacetamide compounds. It also relates to the use of the mixture per se and to a method of controlling weeds.

DISCUSSION OF PRIOR ART

Chloroacetamides are a class of compounds which are known to be suitable for various herbicidal purposes. These include for example, 2-chloroacetamide herbicides such as alachlor (2-chloro-2',6'-diethyl-N-methoxymethylacetanilide), acetochlor (2-chloro-N-ethoxymethyl-6'-ethylacet-o-toluidide), metolachlor [2-chloro-6'-ethyl-N-(2-methoxy-1-methylethyl)acet-o-toluidide] and propachlor (2-chloro-N-isopropylacetanilide), each of which are known from the Pesticide Manual 9th edition (British Crop Protection Council);and dimethenamid [2-chloro-N-(2,4-dimethyl-3-thienyl)-N-(2-methoxy-1-methyl)ethyl-acetamide], which is disclosed in U.S. Pat. No. 4,666,502; and are used pre-emergence or early post-emergence as herbicides for controlling annual grasses and broad leafed weeds in maize, peanuts, soybeans and other crops.

Herbicidal 4-benzoylisoxazoles are disclosed in the literature, for example see European Patent Publication Nos. 0418175, 0487357, 0527036 and 0560482.

Regarding the chloroacetamide herbicides metolachlor and acetochlor, these are typically used for the control of weeds found in maize (corn). The use of these compounds at high dose rates can present problems in terms of maize crop damage, as reported for example by Owen et al., Res. Rep. North Cent. Weed Science Society, Volume 46, page 316 (1989). The problem is particularly prevalent with acetochlor, and typically it is necessary to employ acetochlor in mixture with a safening agent.

Therefore an object of the invention is to provide a herbicidally effective mixture which allows chloroacetamide herbicides such as acetochlor or metolaclor to be used in reduced dose rates whilst retaining both crop selectivity and herbicidal efficacy.

As a result of research and experimentation it has been found that the use of a chloroacetamide herbicide, in combination with certain 4-benzoylisoxazole derivatives, extends the spectrum of herbicidal activity without loss of crop selectivity. Therefore the said combinations represents an important technological advance. The term "combination" as used in this specification refers to the "combination" of a 4-benzoylisoxazole herbicide and a chloroacetamide herbicide.

Surprisingly, in addition to this, it has been found that the combined herbicidal activity of certain 4-benzoylisoxazoles with certain chloroacetamide herbicides for the control of certain weed species e.g. Setaria spp, Abutilon theophrasti, Amaranthus retroflexus, Digitaria sanguinalis, Echinochloa crus-galli, Ipomoea purpurea and Helianthus annuus, and is greater than expected, without an unacceptable increase in crop phytotoxicity, applied pre-emergence (e.g. as a pre-emergence aqueous spray), i.e. the herbicidal activity of the 4-benzoylisoxazole with a chloroacetamide herbicide showed an unexpected degree of synergism, as defined by P. M. L. Tammes, Netherland Journal of Plant Pathology, 70 (1964), pp 73–80 in a paper entitled "Isoboles, a graphic representation of synergism in pesticides".

In addition, the herbicidal activity of the 4-benzoylisoxazoles with a chloroacetamide herbicide shows synergism as defined by Limpel, L. E., P. H. Schuldt and D. Lamont, 1962, 1. Proc. NEWCC 16, 48–53, using the formula:

$$E = X + Y - \frac{X \cdot Y}{100}$$

where

E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic.

This remarkable synergistic effect gives improved reliability in controlling these competitive weeds of many crop species, leading to a considerable reduction in the amount of active ingredient required for weed control.

A high level of control of these weeds is desirable to prevent:

1) yield loss, through competition and/or difficulties with harvest,

2) crop contamination leading to storage and cleaning difficulties, and 3) unacceptable weed seed return to the soil.

DESCRIPTION OF THE INVENTION

The present invention provides method of controlling the growth of weeds at a locus which comprises applying to said locus a herbicidally effective amount of:

(a) a 4-benzoylisoxazole of formula (I):

wherein

R is hydrogen or —CO$_2$R$^3$;

R$^1$ is cyclopropyl;

R$^2$ is selected from halogen, —S(O)$_p$Me and C$_{1-6}$ alkyl or haloalkyl, n is two or three; p is zero, one or two; and R$^3$ is C$_{1-4}$ alkyl; and (b) a chloroacetamide herbicide.

Preferably the chloroacetamide herbicide is of formula (II)

$$Ar—N(R^{21})COCH_2Cl \qquad (II)$$

wherein $R^{21}$ represents hydrogen, $C_{1-6}$ alkyl, haloalkyl, alkoxy or alkoxyalkyl; alkenyl, haloalkenyl, alkynyl, haloalkynyl or acylamidoalkyl having up to six carbon atoms;

Ar represents thienyl or phenyl optionally substituted by one or more groups selected from the group consisting of halogen, amino, $C_{1-6}$ alkyl, haloalkyl, alkoxy and alkoxyalkyl.

In formula (I) above, compounds in which n is three and the groups $(R^2)n$ occupy the 2,3 and 4-positions of the benzoyl ring; or in which n is two and the groups $(R^2)_n$ occupy the 2 and 4- positions of the benzoyl ring are preferred.

In formula (I) above, $R^2$ is preferably selected from halogen (preferably chlorine or bromine), —S(O)$_p$Me and trifluoromethyl.

In formula (I) above, preferably one of the groups $R^2$ is —S(O)$_p$Me.

Compounds in which R is hydrogen are also preferred.

The compounds of formula (I) of particular interest include the following:

A  5-cyclopropyl-4-(2-methylsulphonyl-4-trifluoromethyl)benzoylisoxazole;

B  5-cyclopropyl-4-(4-methylsulphonyl-2-trifluoromethyl)benzoylisoxazole;

C  4-(2-chloro-4-methylsulphonyl)benzoyl-5-cyclopropylisoxazole;

D  4-(4-chloro-2-methylsulphonyl)benzoyl-5-cyclopropylisoxazole; and

E  4-(4-bromo-2-methylsulphonyl)benzoyl-5-cyclopropylisoxazole.

The letters A to E are assigned to these compounds for reference and identification hereafter.

Compound A is particularly preferred.

In formula (II) above, compounds in which $R^{21}$ represents a group selected from methoxymethyl, ethoxymethyl, 2-methoxy-1-methylethyl and 1-methylethyl are preferred.

Compounds of formula (II) above in which Ar represents phenyl or thienyl optionally substituted by one or preferably two groups which may be the same or different selected from ethyl and methyl are also preferred.

The compound of formula (II) in which $R^{21}$ represents methoxymethyl and Ar represents 2,6-diethylphenyl is known as alachlor.

The compound of formula (II) in which $R^{21}$ represents ethoxymethyl and Ar represents 2-ethyl-6-methylphenyl is known as acetochlor.

The compound of formula (II) in which $R^{21}$ represents 2-methoxy-1-methylethyl and Ar represents 2-ethyl-6-methylphenyl is known as metolachlor.

The compound of formula (II) in which $R^{21}$ represents 1-methylethyl and Ar represents phenyl is known as propachlor.

The compound of formula (II) in which $R^{21}$ represents 2-methoxy-1-methylethyl and Ar represents 3-(2,4-dimethyl)thienyl is known as dimethenamid.

The amounts of the chloroacetamide herbicide and 4-benzoylisoxazole applied vary depending on the weeds present and their population, the compositions used, the timing of the application, the climatic and edaphic conditions, and (when used to control the growth of weeds in crop growing areas) the crop to be treated. In general, taking these factors into account, application rates from 0.5 g to 512 g of 4-benzoylisoxazole and from 8 to 4000 g of the chloroacetamide herbicide per hectare give good results. However, it will be understood that higher or lower application rates may be used, depending upon the problem of weed control encountered.

For the selective control of weeds at a locus of weed infestation which is an area used, or to be used, for growing of crops application rates from 0.5 g to 512 g of 4-benzoylisoxazole and from 20 to 4000 g of the chloroacetamide herbicide per hectare are particularly suitable, preferably from 20 to 200 g of 4-benzoylisoxazole and from 200 to 3000 g of the chloroacetamide herbicide per hectare, even more preferably from 25 to 150 g of 4-benzoylisoxazole and from 350 to 2000 g (especially from 450 g to 2000 g) of the chloroacetamide herbicide per hectare.

Where the chloroacetamide herbicide is acetochlor, application rates of from 20 g to 3000 g per hectare of the chloroacetamide herbicide are preferred, more preferably from 150 g to 2000 g, even more preferably from 250 g to 2000 g per hectare, even more preferably from 350 g to 1500 g per hectare, from 450 g to 1500 g per hectare being particularly preferred and from 700 g to 1200 g per hectare is especially preferred.

Where the chloroacetamide herbicide is alachlor or metolachlor, application rates of from 40 g to 4000 g per hectare of the chloroacetamide herbicide are preferred, more preferably from 200 g to 3000 g per hectare, even more preferably from 350 g to 2000 g per hectare, with from 450 g to 2000 g per hectare being especially preferred.

When applied to a crop-growing area, the rate of application should be sufficient to control the growth of weeds without causing substantial permanent damage to the crop.

The method described above may be used to control a very wide spectrum of annual broad-leafed weeds and grass weeds in crops, e.g. maize, without significant permanent damage to the crop. The combined use described above offers both foliar and residual activity and consequently can be employed over a long period of crop development, i.e. from pre-weed pre-crop emergence to post-weed post-crop emergence. In the method according to this feature of the present invention the combined use of (a) and (b) to control grass weeds in maize is preferred. Preferably the herbicides are applied pre-emergence of the weeds and in particular pre-plant incorporated.

In the method described above, the combined use of (a) and (b) in proportions from 1:8000 to 64:1 wt/wt of (a): (b) is preferred, proportions from 1:150 to 1:1 wt/wt being particularly preferred, with proportions from 1:80 to 1:3 wt/wt even more preferred (from 1:80 to 1:2.3 being especially preferred).

By the term 'pre-emergence application' is meant application to the soil in which the weed seeds or seedlings are present before emergence of the crop. One example of a pre-emergence application is known as 'pre-plant incorporated' (PPI), where the herbicide is incorporated into the soil before planting the crop. Another is where the herbicide is applied to the soil surface after sowing the crop. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil.

whereby seedlings present at the time of application or which germinate subsequent to application from seeds present in the soil, are controlled.

In accordance with the usual practice (and a preferred method according to the present invention) a tank mix may be prepared prior to use by combining separate formulations of the individual herbicidal components.

The following non-limiting experiments illustrate the present invention.

EXPERIMENTAL PROCEDURE A

Seed of the various species of broad-leaf or grass weeds were sown in unsterilised clay loam soil in 7 centimeter by 7 centimeter plastic plant pots. The pots were watered and allowed to drain. The soil surface was then sprayed with ranges of concentrations of either the individual herbicide or mixtures of two herbicides in various proportions, dissolved in a 50:50 by volume solution of acetone and water, using a track sprayer set to deliver the equivalent of 290 l/ha. All herbicides were used as unformulated technical materials except dimethenamid, which was used as the commercial formulation "Frontiere" (trade mark), a flowable containing 900 g/l active ingredient; and alachlor, which was used as "Lasso" (trade mark), an emulsifiable concentrate formulation containing 480 g/l active ingredient.

Treated pots were placed at random in four replicate blocks per treatment for each plant species. The pots were held, in a glasshouse, standing on moist capillary matting, under lights and with overhead watering twice daily.

Two weeks after treatment the percent reduction in plant growth, compared to an untreated control, was assessed.

Mean percent reduction in plant growth was calculated for each treatment. Dose/mean response was plotted on Log concentration/Probability graph paper, and lines fitted by eye. For herbicide mixtures a dose/response line for the first herbicide was drawn for each dose rate of the second herbicide and a dose/response line for the second herbicide was drawn for each dose rate of the first herbicide. The doses representing a 90% reduction in plant growth (LD90's) were read from these lines and plotted on graphs whose axes were dose rates of the two herbicides. The line joining these points is an Isobole i.e. a line joining points (mixtures) of equal activity, as described by P. M. L. Tammes, Neth. J. Plant Path. 70 (1964): 73–80. A line was also drawn joining the LD90's of the individual components of the mixture. This line represents the theoretical isobole if the effect of the two components is additive i.e. there is no interaction between them. Isoboles falling below this line indicate synergy between the components while lines lying above it indicate antagonism.

In the tables that follow 'dose' represents the dose rate in grammes per hectare of the active ingredient used; and the figures for the weed control are percentages reduction in growth when compared with the untreated controls.

Results:

TABLE A1

Pre-Emergence treatment of *Setaria viridis* with various mixtures of Compound A and metolachlor

| | | Metolachlor | | | | | |
|---|---|---|---|---|---|---|---|
| Cpd. | Dose | 0 | 2 | 4 | 8 | 16 | 32 | 64 |
| A | 0 | — | 5 | 22.5 | 38.75 | 61.25 | 87.5 | 98 |
| | 0.5 | 15 | 27.5 | 36.25 | 38.75 | 70 | 91.25 | 98.25 |
| | 1 | 5 | 31.25 | 15 | 55 | 67.5 | 87.5 | 98.25 |
| | 2 | 47.5 | 20 | 17.5 | 35 | 66.25 | 78.75 | 100 |

TABLE A1-continued

Pre-Emergence treatment of *Setaria viridis* with various mixtures of Compound A and metolachlor

| | | Metolachlor | | | | | |
|---|---|---|---|---|---|---|---|
| Cpd. | Dose | 0 | 2 | 4 | 8 | 16 | 32 | 64 |
| | 4 | 33.75 | 17.5 | 10 | 27.5 | 80 | 94.75 | 98.75 |
| | 8 | 38.75 | 25 | 42.5 | 55 | 71.25 | 95 | 98.5 |
| | 16 | 53.75 | 45 | 57.25 | 55 | 82.5 | 93.75 | 97.25 |
| | 32 | 70 | 75 | 80 | 76 | 95 | 96 | 99.75 |
| | 64 | 76 | 88.75 | 91.25 | 93.5 | 95 | 100 | 98.75 |
| | 128 | 88.75 | 96.25 | 98.75 | 97.25 | 100 | 100 | 100 |

TABLE A2

Pre-Emergence treatment of *Amaranthus retroflexus* with various mixtures of Compound A and metolachor

| Cpd. | | Metolachlor | | | | | |
|---|---|---|---|---|---|---|---|
| A | Dose | 0 | 31.25 | 62.5 | 125 | 250 | 500 |
| | 0 | — | 46.25 | 53.75 | 35 | 85 | 95 |
| | 1 | 12.5 | 22.5 | 70 | 78.75 | 92.5 | 72.25 |
| | 2 | 51.25 | 43.75 | 80 | 66.25 | 97.25 | 100 |
| | 4 | 12.5 | 80 | 93.75 | 98.75 | 83.75 | 99.75 |
| | 8 | 87.5 | 93.75 | 97.5 | 91.25 | 95 | 98.75 |
| | 16 | 92.5 | 97 | 96.25 | 99.75 | 93.75 | 98.75 |
| | 32 | 99.75 | 98.75 | 98.75 | 100 | 100 | 100 |
| | 64 | 99.75 | 99.75 | 97 | 100 | 100 | 100 |

TABLE B1

Pre-Emergence treatment of *Digitaria sanguinalis* with various mixtures of Compound A and alachlor

| | | Alachlor | | | | | |
|---|---|---|---|---|---|---|---|
| Cpd. | Dose | 0 | 4 | 8 | 16 | 32 | 64 | 128 |
| A | 0 | — | 0 | 25 | 6.25 | 37.5 | 75 | 95 |
| | 1 | 18.75 | 15 | 22.5 | 15 | 10 | 75 | 82.5 |
| | 2 | 20 | 27.5 | 30 | 36.25 | 22.5 | 60 | 93.75 |
| | 4 | 33.75 | 38.75 | 30 | 50 | 38.75 | 71.25 | 96 |
| | 8 | 67.5 | 55 | 66.285 | 62.5 | 82.5 | 83.75 | 67.5 |
| | 16 | 50 | 94.75 | 87.25 | 94.5 | 71.25 | 85 | 95 |
| | 32 | 73.5 | 91.25 | 95 | 87.5 | 87.25 | 99.75 | 98.5 |
| | 64 | 87.5 | 91.25 | 93.75 | 99.75 | 99.75 | 95 | 100 |

Table B2

Pre-Emergence treatment of *Echinochloa crus-galli* with various mixtures of Compound A and alachlor

| | | Alachlor | | | | | |
|---|---|---|---|---|---|---|---|
| Cpd. | Dose | 0 | 4 | 8 | 16 | 32 | 64 | 128 |
| A | 0 | — | 18.75 | 5 | 12.5 | 46.25 | 91.25 | 98.75 |
| | 1 | 12.5 | 12.5 | 10 | 17.5 | 77.5 | 91.25 | 99.75 |
| | 2 | 6.25 | 0 | 21.25 | 12.5 | 67.5 | 91.25 | 97.5 |
| | 4 | 1.25 | 15 | 32.5 | 11.25 | 77.5 | 95 | 90 |
| | 8 | 61.25 | 43.75 | 58.75 | 80 | 80 | 100 | 100 |
| | 16 | 71.25 | 56.25 | 60 | 81.25 | 92.5 | 97.25 | 98.75 |
| | 32 | 75 | 73.5 | 85 | 90 | 97.5 | 98.5 | 100 |
| | 64 | 93.5 | 98.5 | 97.5 | 82.25 | 98.5 | 99.75 | 98.75 |
| | 128 | 93.75 | 95.75 | 100 | 96.25 | 97 | 97.5 | 100 |

TABLE C1

Pre-Emergence treatment of *Digitaria sanguinalis* with various mixtures of Compound A and dimethenamid

| Cpd | Dose | 0 | 4 | 8 | 16 | 32 | 64 | 128 | 256 |
|---|---|---|---|---|---|---|---|---|---|
| A | 0 | — | 16.25 | 15 | 77.5 | 89.75 | 98.25 | 92.5 | 98.75 |
|   | 2 | 20 | 3.75 | 30 | 61.25 | 77.5 | 83.75 | 97 | 99.5 |
|   | 4 | 40 | 43.75 | 35 | 62.5 | 83.5 | 94.25 | 97.5 | 99.75 |
|   | 8 | 7.5 | 46.25 | 63.75 | 82.5 | 92.25 | 97.25 | 95 | 100 |
|   | 16 | 50 | 73.25 | 69.5 | 78.75 | 94.5 | 93.75 | 99.75 | 100 |
|   | 32 | 74.75 | 91 | 93.5 | 95 | 93.75 | 100 | 99.75 | 100 |
|   | 64 | 80 | 96 | 93.75 | 92 | 87.5 | 88.5 | 97.5 | 99.75 |
|   | 128 | 93.5 | 93.75 | 85 | 95 | 99.75 | 100 | 94.75 | 100 |

TABLE C2

Pre-Emergence treatment or *Echinochloa crus-galli* with various mixtures of Compound A and dimethenamid

| Cpd. | Dose | 0 | 4 | 8 | 16 | 32 | 64 | 128 |
|---|---|---|---|---|---|---|---|---|
| A | 0 | — | 17.5 | 38.75 | 81.25 | 93.5 | 97.5 | 100 |
|   | 2 | 3.75 | 15 | 56.25 | 91 | 98.75 | 99.5 | 100 |
|   | 4 | 2.5 | 58.75 | 73.75 | 91.25 | 90 | 98.5 | 97.5 |
|   | 8 | 32.5 | 52.5 | 81.25 | 96.25 | 100 | 99.5 | 100 |
|   | 16 | 60 | 76.25 | 90 | 95 | 98.75 | 99.75 | 100 |
|   | 32 | 90 | 89.75 | 98.5 | 91.25 | 99.5 | 100 | 100 |
|   | 64 | 97 | 92.5 | 94.75 | 97.5 | 100 | 100 | 98.75 |
|   | 128 | 99.75 | 99.25 | 99.5 | 99.75 | 100 | 98.75 | 100 |

TABLE D1

Pre-emergence treatment of *Digitaria sanguinalis* with various mixtures of Compound A and acetochlor

| Cpd. | Dose g/ha | 0 | 3.75 | 7.5 | 15 | 30 | 60 | 120 | 240 |
|---|---|---|---|---|---|---|---|---|---|
| A | 0 | — | 0 | 0 | 7.5 | 32.5 | 85 | 100 | 98.75 |
|   | 1 | 0 | 0 | 5 | 20 | 42.5 | 75 | 95 | 100 |
|   | 2 | 12.5 | 7.5 | 15 | 32.5 | 51.25 | 91.25 | 97.5 | 98.75 |
|   | 4 | 17.5 | 7.5 | 15 | 35 | 68.75 | 83.75 | 99.5 | 100 |
|   | 8 | 61.25 | 38.75 | 53.75 | 58.75 | 79.75 | 85 | 98.75 | 100 |
|   | 16 | 67.5 | 53.75 | 73.25 | 71.25 | 73.5 | 97.5 | 99.75 | 100 |
|   | 32 | 66 | 88.5 | 76 | 91.25 | 89.75 | 94.75 | 98.75 | 100 |
|   | 64 | 95 | 75 | 99.5 | 92.5 | 98.75 | 95 | 97.5 | 100 |
|   | 128 | 76.25 | 97.25 | 93.75 | 100 | 97.5 | 98.75 | 98.75 | 100 |
|   | 256 | 98.75 | 98.75 | 93.75 | 98.5 | 100 | 100 | 98.75 | 100 |

TABLE D2

Pre-emergence treatment of *Echinochloa crus-galli* with various mixtures of Compound A and acetochlor

| Cpd. | Dose g/ha | 0 | 3.75 | 7.5 | 15 | 30 | 60 | 120 | 240 |
|---|---|---|---|---|---|---|---|---|---|
| A | 0 | — | 12.5 | 36.25 | 55 | 88.75 | 98.75 | 98.75 | 100 |
|   | 1 | 11.25 | 27.5 | 27.5 | 37.5 | 81.25 | 100 | 100 | 100 |
|   | 2 | 7.5 | 6.25 | 20 | 57.5 | 92.5 | 97.25 | 100 | 100 |
|   | 4 | 15 | 20 | 23.75 | 70 | 93.75 | 98.5 | 100 | 100 |
|   | 8 | 15 | 27.5 | 73.75 | 78.75 | 98.75 | 99.75 | 100 | 100 |
|   | 16 | 62.5 | 77.5 | 63.5 | 91.25 | 100 | 100 | 100 | 100 |
|   | 32 | 86 | 91.25 | 93.5 | 98.75 | 95 | 100 | 100 | 100 |
|   | 64 | 87.5 | 98.75 | 100 | 98.75 | 98.75 | 100 | 100 | 100 |

TABLE D2-continued

Pre-emergence treatment of *Echinochloa crus-galli* with various mixtures of Compound A and acetochlor

| Cpd. | Dose g/ha | 0 | 3.75 | 7.5 | 15 | 30 | 60 | 120 | 240 |
|---|---|---|---|---|---|---|---|---|---|
|   | 128 | 99.5 | 98.5 | 99.5 | 99.75 | 100 | 100 | 100 | 100 |
|   | 256 | 92.5 | 81.25 | 98.5 | 96.25 | 98.5 | 99.75 | 100 | 100 |

BRIEF DESCRIPTION OF THE DRAWINGS

FIG. I is an LD90 isobole plot calculated from observed values (-*-) and a corresponding plot of expected additive values (dashed line) for a range of mixtures of Compound A with metolachlor against the weed species *Setaria viridis*, produced from the results shown in Table A1;

FIG. II is an LD90 isobole plot calculated from observed values (-*-) and a corresponding plot of expected additive values (dashed line) for a range of mixtures of Compound A with metolachlor against the weed species *Amaranthus retroflexus*, produced from the results shown in Table A2;

FIG. III is an LD90 isobole plot calculated from observed values (-*-) and a corresponding plot of expected additive values (dashed line) for a range of mixtures of Compound A with alachlor against the weed species *Digitaria sanguinalis*, produced from the results shown in Table B1;

FIG. IV is an LD90 isobole plot calculated from observed values (-*-) and a corresponding plot of expected additive values (dashed line) for a range of mixtures of Compound A with alachlor against the weed species *Echinochloa crus-galli*, produced from the results shown in Table B2;

FIG. V is an LD90 isobole plot calculated from observed values (-*-) and a corresponding plot of expected additive values (dashed line) for a range of mixtures of Compound A with dimethenamid against the weed species *Digitaria sanguinalis*, produced from the results shown in Table C1;

FIG. VI is an LD90 isobole plot calculated from observed values (-*-) and a corresponding plot of expected additive values (dashed line) for a range of mixtures of Compound A with dimethenamid against the weed species *Echinochloa crus-galli*, produced from the results shown in Table C2.

FIG. VII is an LD90 isobole plot calculated from observed values (-*-) and a corresponding plot of expected additive values (dashed line) for a range of mixtures of Compound A with acetochlor against the weed species *Digitaria sanguinalis*, produced from the results shown in Table D1;

FIG. VIII is an LD90 isobole plot calculated from observed values (-*-) and a corresponding plot of expected additive values (dashed line) for a range of mixtures of Compound A with acetochlor against the weed species *Echinochloa crus-galli*, produced from the results shown in Table D2.

Figure 1:
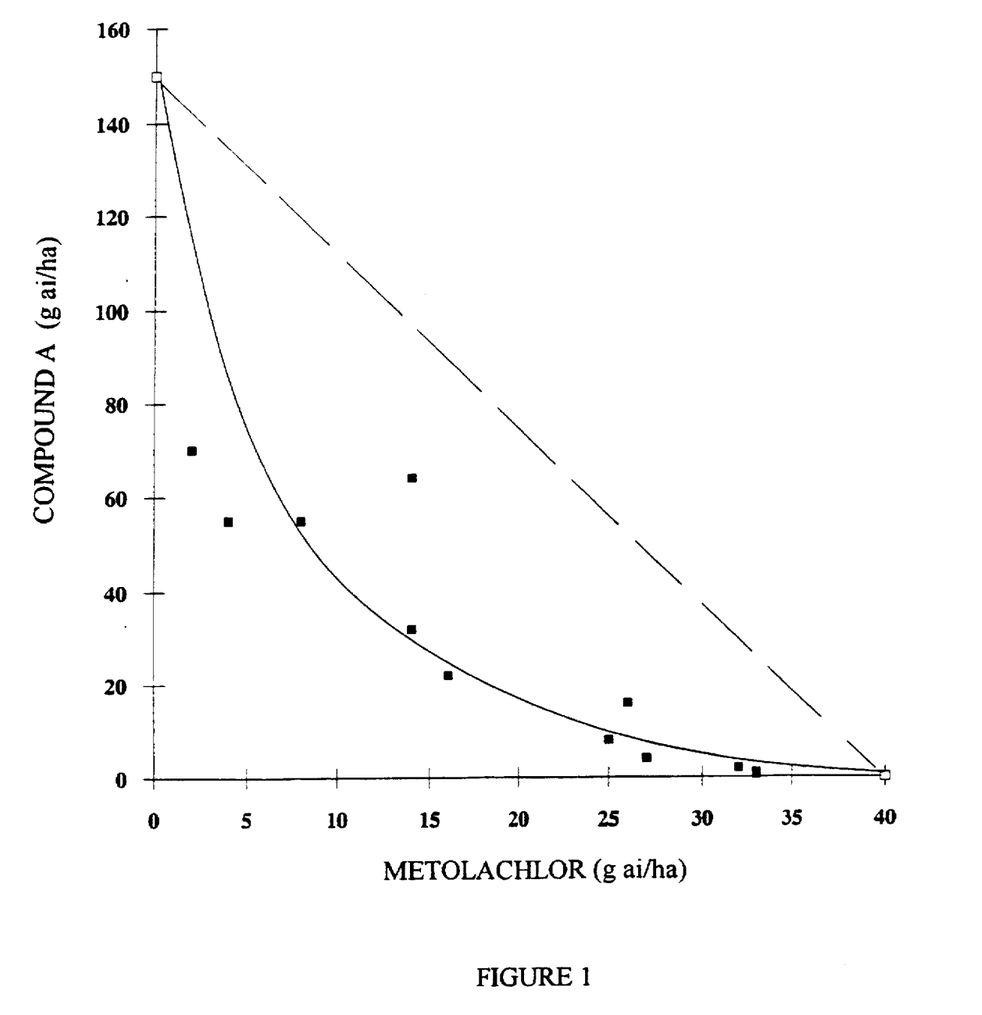
Figure 2:
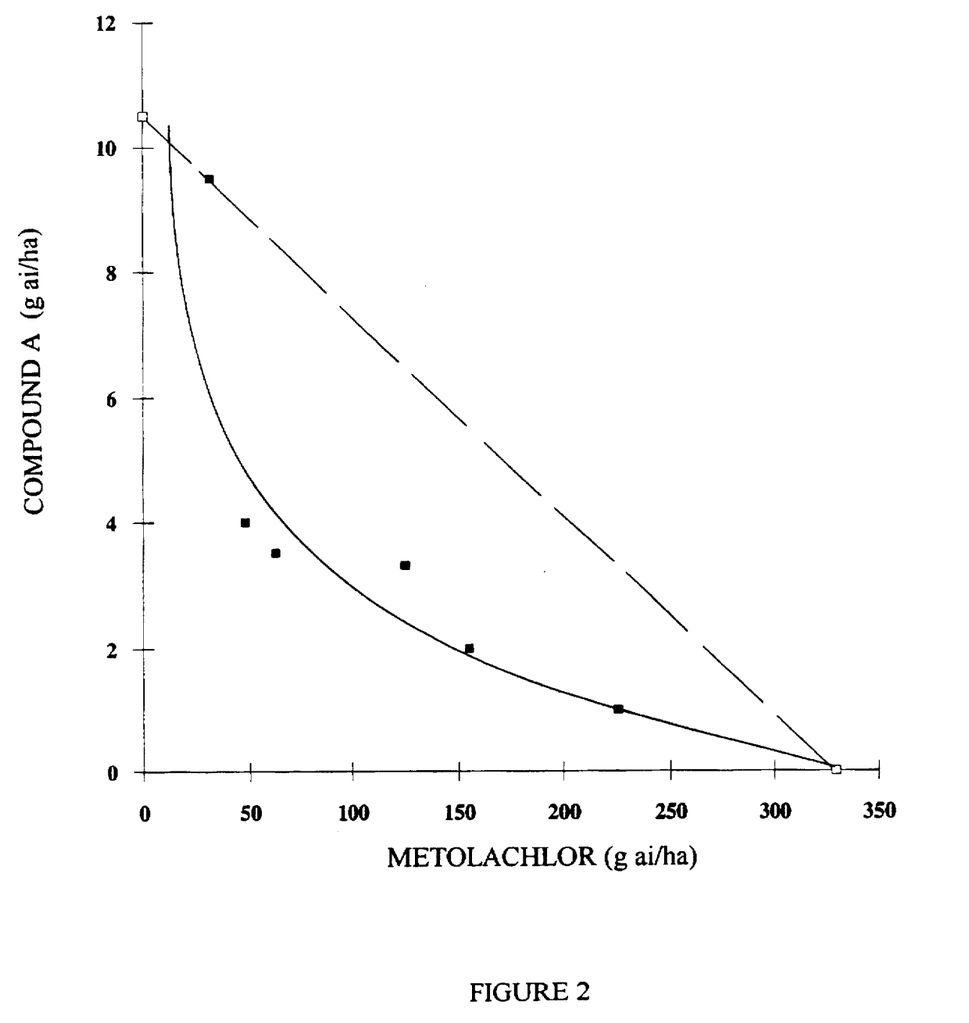
Figure 3:
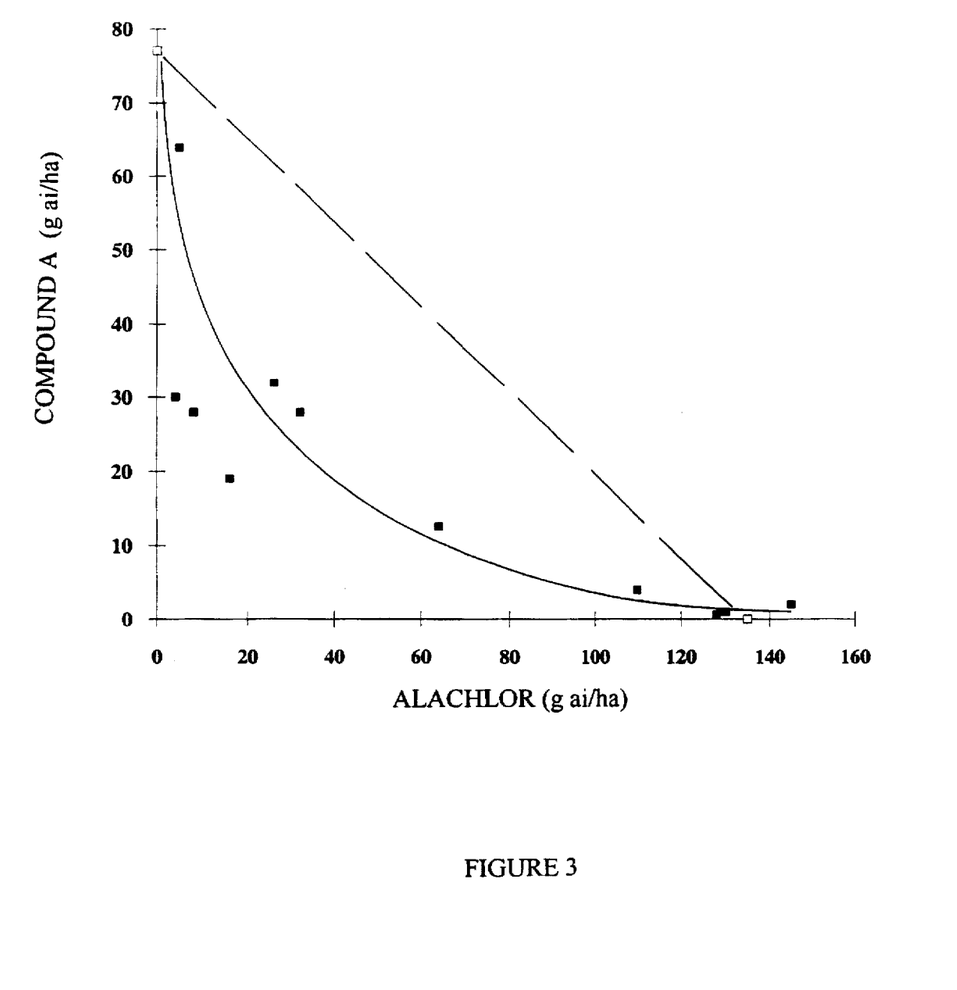
Figure 4:
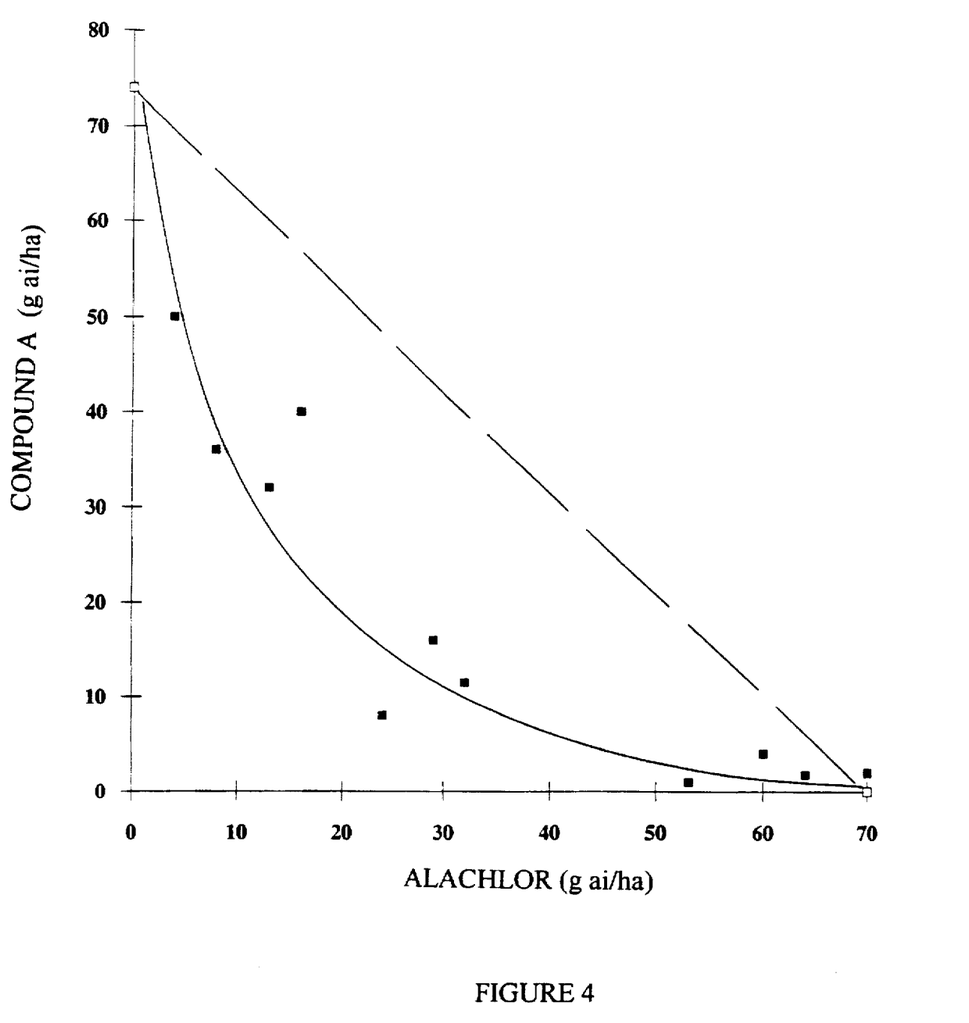
Figure 5:
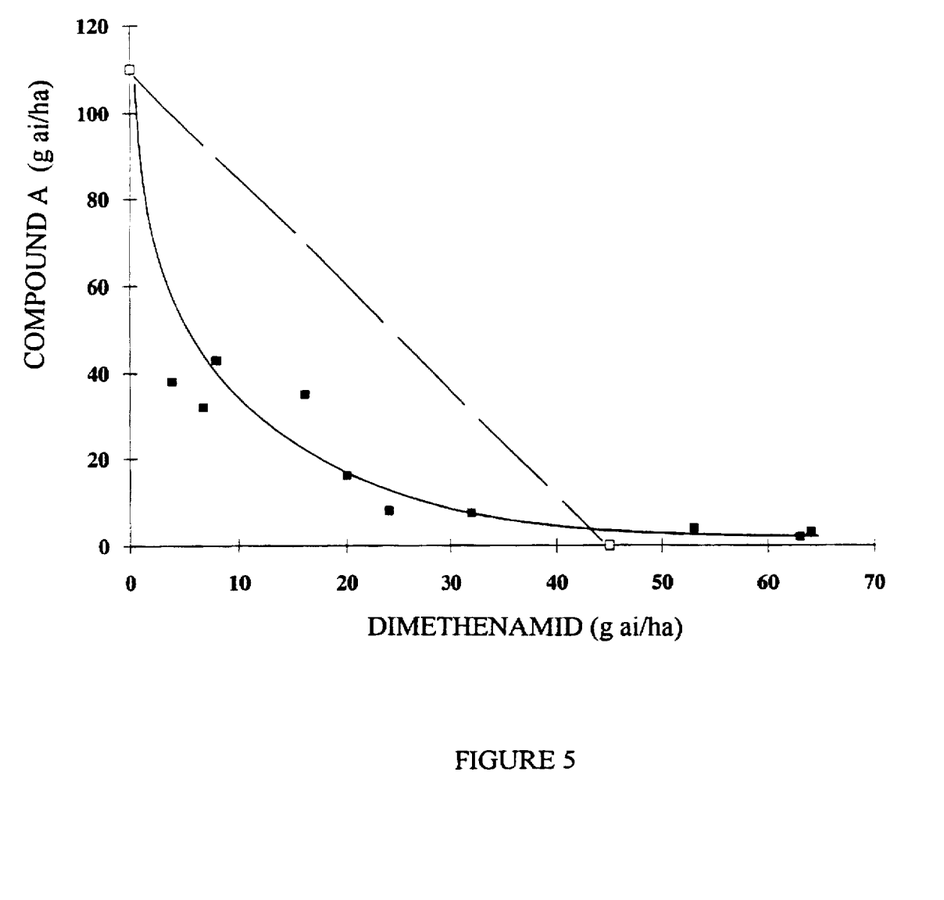
Figure 6:
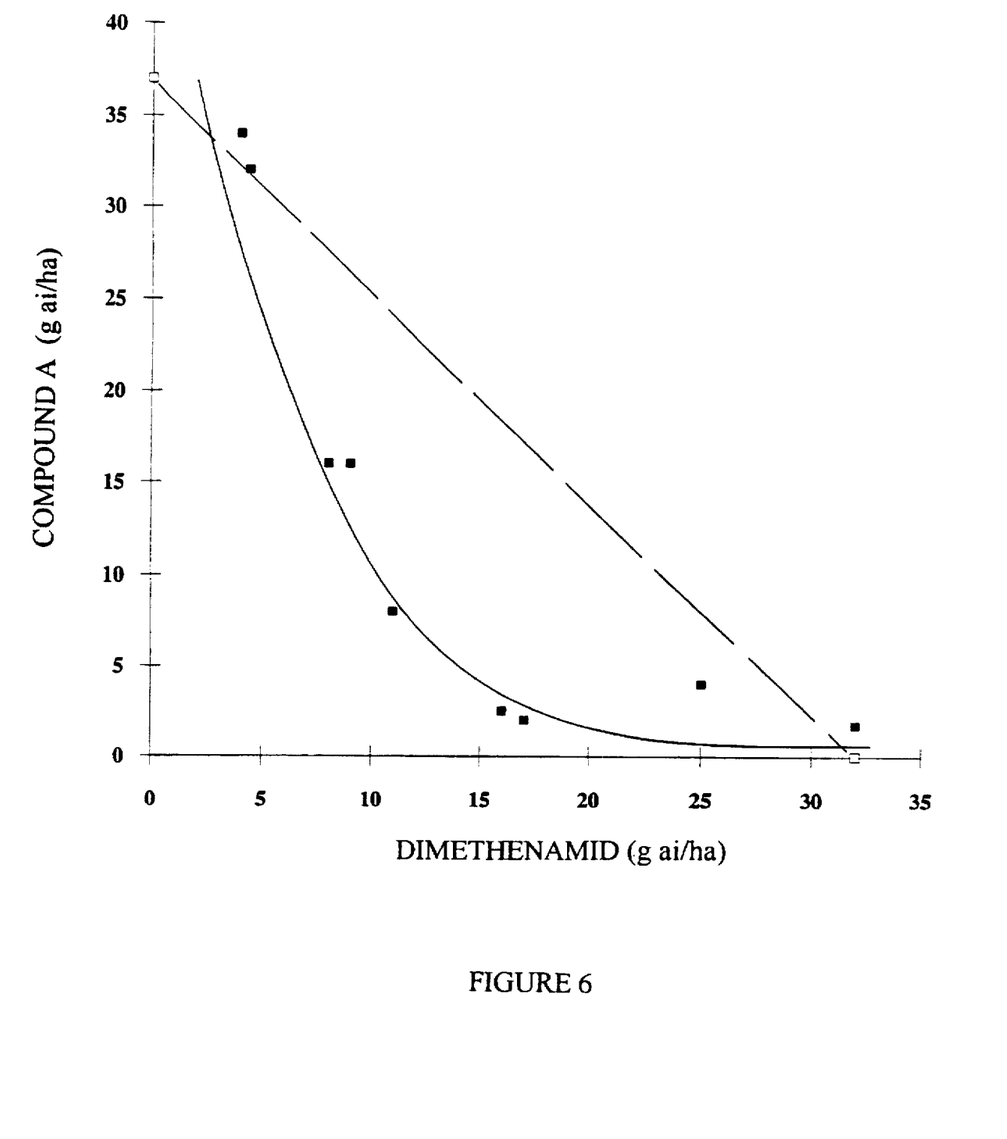
Figure 7:
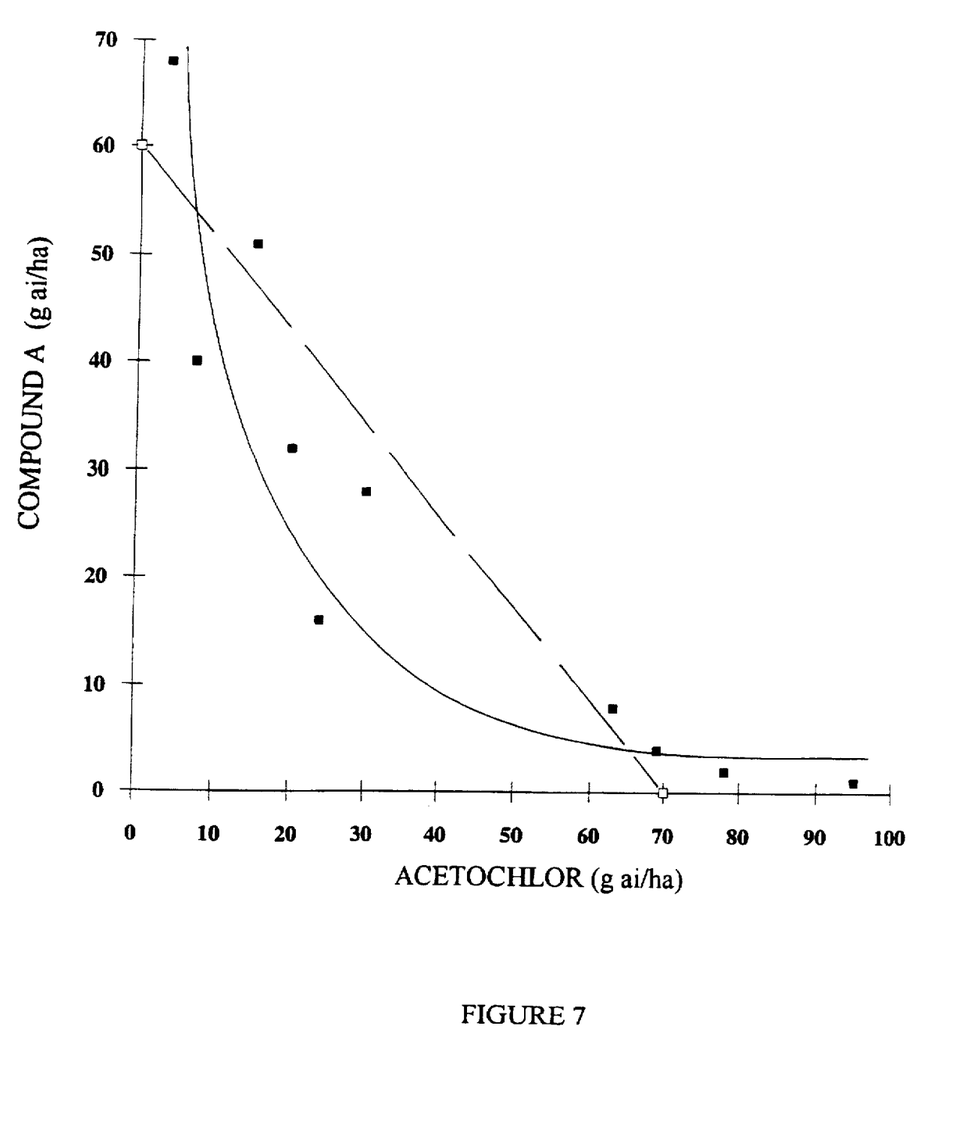
Figure 8:
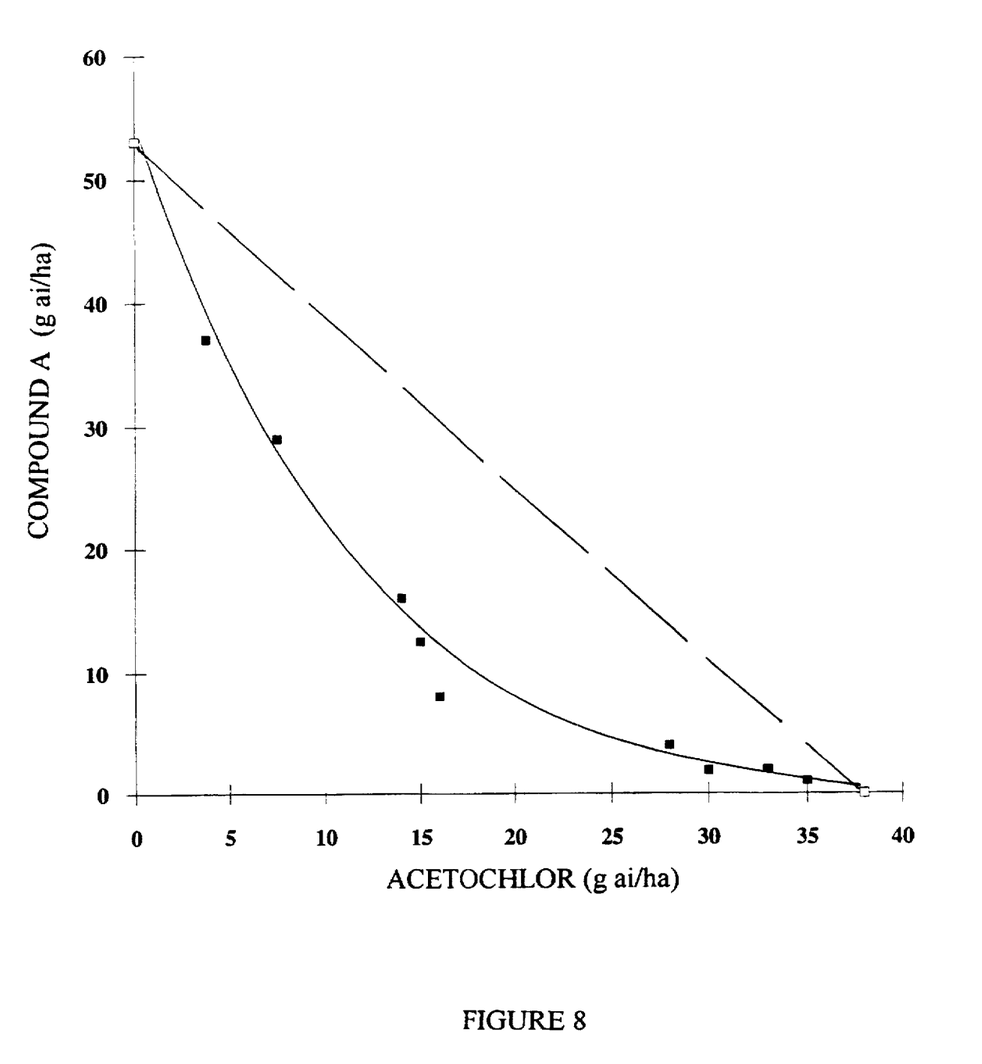

The results above clearly demonstrate the excellent and unexpected degree of synergism obtained with the combination of the invention.

The isoboles produced from the above data, shown hereinafter in FIGS. I to VIII were clearly type III curves (Tammes op. cit. Page 75, FIG. 2) characteristic of synergism.

EXPERIMENTAL PROCEDURE B

The experiments were carried out pre-emergence of the weed species at (i) a research farm in Brazil with Compounds B and C (each formulated as a wettable powder) and metolachlor, (formulated as a suspension concentrate); and (ii) in research farms in the Mid West corn belt of the United States with compound D (formulated as a wettable powder) and metolachlor (formulated as a suspension concentrate).

A solution of the two active ingredients (a.i.) was mixed for one hour and applied at a spray volume of 231 liters/hectare to a 3 meter by 5 meter test plot comprising the weed species which were sown 2 days earlier. 3 replicates were performed. A control plot was sprayed with a solution not containing test compound. Visual assessment of phytotoxicity was made after 36 or 40 days from sowing each weed species based on a comparison with the control plot.

The tables below show the observed percentage control of the weed species by each combination, with the figure in brackets representing the predicted value using the Limpel formula. The dose rates are in grammes per hectare.

Table E1

Pre-Emergence treatment of *Abutilon theophrasti* with various mixtures of Compound B and metolachlor

| Cpd. | | Metolachlor | |
|---|---|---|---|
| B | Dose | 0 | 1000 |
| | 0 | — | 0 |
| | 50 | 75 | 98 (75) |

TABLE E2

Pre-Emergence treatment of *Abutilon theophrasti* with various mixtures of Compound C and metolachlor

| Cpd. | | Metolachlor | |
|---|---|---|---|
| C | Dose | 0 | 1000 |
| | 0 | — | 0 |
| | 50 | 73 | 95 (73) |

TABLE E3

Pre-Emergence treatment of *Amaranthus retroflexus* with various mixtures of Compound D and metolachlor

| Cpd. | | Metolachlor | |
|---|---|---|---|
| | 1st Research Farm | | |
| D | Dose | 0 | 480 |
| | 0 | — | 38 |
| | 37.5 | 38 | 85 (62) |
| | 2nd Research Farm | | |
| D | Dose | 0 | 480 |
| | 0 | — | 78 |
| | 37.5 | 10 | 100 (80) |
| | 3rd Research Farm | | |
| D | Dose | 0 | 480 |
| | 0 | — | 91 |
| | 37.5 | 10 | 98 (92) |

TABLE E4

Pre-Emergence treatment of *Setaria faberii* with various mixtures of Compound D and metolachlor

| Cpd. | | Metolachlor | |
|---|---|---|---|
| | 1st Research Farm | | |
| D | Dose | 0 | 480 |
| | 0 | — | 91 |
| | 37.5 | 22 | 96 (93) |
| | 2nd Research Farm | | |
| D | Dose | 0 | 480 |
| | 0 | — | 84 |
| | 37.5 | 62 | 100 (97) |
| | 3rd Research Farm | | |
| D | Dose | 0 | 480 |
| | 0 | — | 84 |
| | 37.5 | 32 | 98 (89) |

EXPERIMENTAL PROCEDURE C

The experiments were carried out pre-emergence of the weed species at various research farm locations throughout the Mid-West corn belt in United States of America with Compounds A and D (each formulated as wettable powders) and metolachlor (formulated as a 96% emulsifiable concentrate), alachlor (formulated as a 48% emulsifiable concentrate) and dimethenamid (formulated as a 90% emulsifiable concentrate).

Various mixtures of the above 4-benzoylisoxazoles and chloroacetamides were weighed out and dissolved in water to give a solution containing the appropriate concentrations and ratios of active ingredients.

The solution was mixed for one hour and applied at a spray volume of 231 liters/hectare to a 3 meter by 5 meter test plot comprising the maize seed which were sown 2 days earlier. 3 replicates were performed. The experiments were performed using seven varities of maize (except for the mixtures comprising alachlor at 1120 g per hectare, where four varieties were used). A control plot was sprayed with a solution not containing test compound. Visual assessment of phytotoxicity was made 40 days after sowing the maize seeds based on a comparison with the control plot.

TABLE F1

Field trial showing the biological interaction between Compound A and metolachlor on maize

| Cpd | | Metolachlor | | |
|---|---|---|---|---|
| A | Dose | 0 | 560 | 1120 |
| | 0 | — | — | — |
| | 78 | 0 | 0 | 0 |
| | 105 | 0 | 0 | 0 |

TABLE F2

Field trial showing the biological interaction between Compound A and alachlor on maize

| Cpd | | | Alachlor | |
|-----|------|---|----------|------|
|     |      | 0 | 560      | 1120 |
| A   | Dose 0 | — | —      | —    |
|     | 78   | 0 | 0        | 0    |
|     | 105  | 0 | 0        | 0    |

TABLE F3

Field trial showing the biological interaction between Compound A and dimethenamid on maize

| Cpd | | | Dimethenamid | |
|-----|------|---|------|-----|
|     |      | 0 | 336  | 672 |
| A   | Dose 0 | — | —  | —   |
|     | 78   | 0 | 0    | 0   |
|     | 105  | 0 | 0    | 0   |

EXPERIMENTAL PROCEDURE D

The following experiments were carried out pre-emergence of the weed species. Compound A, formulated as a wettable dispersible granule as described in Example 1 herebelow (750 g per kilogram) and each of acetochlor (used as the commercially available formulation "Harness" (trade mark), an emulsifiable concentrate containing 960 g of acetochlor per kilogram, and which also contains the safening agent flurazole), metolachlor (used as the commercially available formulation "Duelor" (trade mark), an emulsifiable concentrate containing 960 g of metolachlor per kilogram), alachlor (used as the commercially available formulation "Lasso" (trade mark), an emulsifiable concentrate containing 480 g of alachlor per kilogram) and dimethenamid (used as the commercially available formulation "Frontiere" (trade mark), a flowable containing 900 g/l active ingerident) were dissolved in water and sprayed at a volume rate of 187 liters/hectare on various test plots (10 square meters in area) either alone or in mixtures. The soil was a clay-loam, with a pH of 7, the experiments being conducted in June in Volga, Brookings, U.S.A. The various weed and crop species were drill sown and the various compositions were applied on the same day after drilling. Three replicates were performed and the efficacy of the various mixtures were determined by visual assessment of the percentage phytotoxicity in comparison with an untreated control. Assessment was made about 26 days after treatment. In the Tables which follow the dose is expressed in grammes per hectare and the figures in brackets represent the expected results according to the Colby formula.

Results

TABLE G1

Pre-emergence treatment of *Abutilon theophrasti* with mixtures of Compound A and various chloroacetamide herbicides

| Cpd |        |    | Acetochlor | Metolachlor | Alachlor | Dimethenamid |
|-----|--------|----|-----------|-------------|----------|--------------|
| A   | Dose   | 0  | 480       | 480         | 480      | 200          |
|     |        | 0  | 35        | 10          | 20       | 12           |
|     |        | 37.5 | 93 | 100 (95) | 100 (94) | 9  7 (94) | 100 (94) |

TABLE G2

Pre-emergence treatment of *Helianthus annuus* with mixtures of Compound A and various chloroacetamide herbicides

| Cpd |      |    | Acetochlor | Metolachlor | Alachlor | Dimethenamid |
|-----|------|----|-----------|-------------|----------|--------------|
| A   | Dose | 0  | 480       | 480         | 480      | 200          |
|     |      | 0  | 10        | 3           | 3        | 3            |
|     |      | 37.5 | 18 | 38 (26) | 23 (20) | 3  2 (20) | 40 (20) |

TABLE G3

Pre-emergence treatment of *Panicum miliaceum* with mixtures of Compound A and various chloroacetamide herbicides

| Cpd |      |    | Acetochlor | Metolachlor | Alachlor | Dimethenamid |
|-----|------|----|-----------|-------------|----------|--------------|
| A   | Dose | 0  | 480       | 480         | 480      | 200          |
|     |      | 0  | 72        | 52          | 53       | 27           |
|     |      | 37.5 | 65 | 94 (90) | 93 (83) | 63 (84) | 99 (75) |

TABLE G4

Pre-emergence treatment of maize (*Zea mays*) with mixtures of Compound A and various chloroacetamide herbicides

| Cpd |      |    | Acetochlor | Metolachlor | Alachlor | Dimethenamid |
|-----|------|----|-----------|-------------|----------|--------------|
| A   | Dose | 0  | 480       | 480         | 480      | 200          |
|     |      | 0  | 0         | 0           | 0        | 0            |
|     |      | 37.5 | 0 | 0 | 0 | 0 | 0 |

It will be understood that the results presented in Experimental Procedures B to D were obtained in field trials. Such trials generally represent a more rigorous test of herbicidal properties than tests in the greenhouse, where test plants are protected from the variable conditions to which they are inevitably subject in the open field. Because of the variability of conditions in field tests, it is generally more difficult to secure a clear showing of synergism than in greenhouse testing. Nevertheless, herbicidal mixtures which demonstrate synergism in greenhouse testing must, if they are to be of commercial utility, be capable of demonstrating synergism under field conditions, i.e. under the conditions which will prevail when they are used by a farmer. The results obtained in the foregoing Examples therefore represent a particularly clear demonstration of synergism under practical conditions.

According to a further feature of the present invention there are provided herbicidal compositions comprising (a) a 4-benzoylisoxazole derivative of formula I as defined above;and (b) a chloroacetamide herbicide;

in association with, and preferably homogeneously dispersed in a herbicidally acceptable diluent or carrier and/or surface active agent.

The term "herbicidal composition" is used in a broad sense, to include not only compositions which are ready for use as herbicides but also concentrates which must be diluted before use. Preferably, the compositions contain from 0.05 to 90% by weight of 4-benzoylisoxazole and chloroacetamide herbicide.

Unless otherwise stated, the percentages and ratios appearing in this specification are by weight.

Generally a composition in which the ratio of (a):(b) is from 1:8000 to 64:1 wt/wt of (a):(b) is preferred, proportions from 1:150 to 1:1 wt/wt being particularly preferred, with proportions from 1:80 to 1:3 wt/wt even more preferred (from 1:80 to 1:2.3 wt/wt being especially preferred).

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

The wettable powders (or powders for spraying) usually contain from 20 to 95% of 4-benzoylisoxazole and chloroacetamide herbicide, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking agents and colourings.

The aqueous suspension concentrates, which are applicable by spraying, are prepared in such a way as to obtain a stable fluid product (by fine grinding) which does not settle out and they usually contain from 10 to 75% of 4-benzoylisoxazole and chloroacetamide herbicide, from 0.5 to 15% of surface acting agents, from 0.1 to 10% of thixotropic agents, from 0 to 10% of suitable additives such as antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Preferred herbicidal compositions according to the present invention are wettable powders and water-dispersible granules.

Herbicidal compositions according to the present invention may also comprise a 4-benzoylisoxazole and a chloroacetamide in association with one or more other pesticidally active compounds and, if desired one or more compatible pesticidally acceptable diluents and carriers. Preferred herbicidal compositions according to the present invention are those which comprise a 4-benzoylisoxazole and a chloroacetamide herbicide in association with other herbicides.

The following is an example of a composition suitable for use in the method of the invention. In the description that follows the following are trade marks: REAX, Sellogen, Barden, Aerosil, Igepal, Rhodafac, Biodac.

Example C1

The following composition was prepared as a wettable dispersible granule (the percentages that follow are by weight):

| | |
|---|---|
| 4-Benzoylisoxazole (Compound A): | 75.0% |
| REAX 88A (Surfactant): | 10.0% |
| Sellogen HR (Surfactant): | 3.0% |
| Barden AG-1 (Clay): | 11.0% |
| Aerosil R972 (Silica filler) | 1.0% |

This was used in tank mixtures with various chloroacetamide herbicides, as hereinbefore described.

The compositions of the invention may be made up as an article of manufacture comprising a 4-benzoylisoxazole and a chloroacetamide herbicide and optionally other pesticidally active compounds as hereinbefore described, and as is preferred, a herbicidal composition as hereinbefore described and preferably a herbicidal concentrate which must be diluted before use, comprising the 4-benzoylisoxazole and chloroacetamide within a container for the aforesaid 4-benzoylisoxazole and chloroacetamide or a said herbicidal composition and instructions physically associated with the aforesaid container, setting out the manner in which the aforesaid 4-benzoylisoxazole and chloroacetamide or herbicidal composition contained therein, is to be used to control the growth of weeds. The containers will normally be of the types conventionally used for the storage of chemical substances and concentrated herbicidal compositions, which are solids or liquids at normal ambient temperatures, for example cans and drums of plastics materials or metal (which may be internally-lacquered), bottles of glass and plastics materials; and when the contents of the container is a solid, for example a granular herbicidal composition, boxes, for example of cardboard, plastics material, metal or sacks. The containers will normally be of sufficient capacity, to contain amounts of the active ingredients or herbicidal compositions sufficient to treat at least one hectare of ground, to control the growth of weeds therein but will not exceed a size which is convenient for conventional methods of handling. Instructions will be physically associated with the container, for example by being printed directly thereon or on a label or tag affixed thereto. The directions will normally indicate that the contents of the container, after dilution if necessary, are to be applied to control the growth of weeds at rates of application from 0.5 to 512 g of 4-benzoylisoxazole and from 8 to 4000 g of chloroacetamide herbicide per hectare in the manner and for the purpose hereinbefore described.

According to a further feature of the present invention, there is provided a product comprising (a)

4-benzoylisoxazole of formula I above and (b) a chloroacetamide herbicide, as a combined preparation for simultaneous, separate or sequential use in controlling the growth of weeds at a locus.

According to a further feature of the present invention, the compositions of the invention may be provided in a water soluble package comprising an isoxazole derivative of formula I as defined above and a chloroacetamide herbicide, wherein the isoxazole derivative and the chloroacetamide herbicide are not in physical contact with each other until the contents of the package are released. This offers the advantage that any incompatability problems which may exist between the different components, for example if mixed together in high concentrations, are avoided. By way of example, the isoxazole derivative may be formulated as a wettable powder or water dispersible granule and sealed within a first water soluble package, and said first water soluble package may be placed within a second water soluble package containing the chloroacetamide herbicide, preferably formulated as an emulsifiable concentrate or emulsifiable gel. The second package is then sealed by known methods (for example by heat sealing to provide a water soluble bag within a water soluble bag). Alternatively, the two components may be provided in adjacent compartments of the water soluble package. Examples of water soluble packages suitable for containing the compositions described above are found in European Patent Publication Nos. 0577702 and 0608340, and U.S. Pat. Nos. 5,222,595; 5224,601; 5,351,831; and 5,323,906.

The processes described in European Patent Publication Nos. 0418175, 0487357, 0527036 and 0560482 may be used to prepare the compounds of formula (I).

Acetochlor was prepared according to the following procedure:

Synthesis of (N-chloroacetyl-N-ethoxymethyl-2-ethyl-6-methylaniline (acetochlor)

Chloroacetyl chloride (84.8 g) was added, over 20 minutes, to a solution of 2-ethyl-6-methylaniline (67.5 g), glacial acetic acid (230 ml), sodium acetate (anhydrous 110.5 g) in water (200 ml) at such a rate that the reaction temperature did not exceed 10° C. The resulting suspension was then stirred vigorously for 30 minutes at 10° C. (requiring the addition of further quantities of acetic acid and water to maintain fluidity). The suspension was filtered, the resulting solid was air-dried on the filter and was then recrystallised from ethanol/water to yield the N-chloroacetyl-2-ethyl-6-methylaniline as a colourless solid (58.7 g), m.p. 122°–123° C. This product (10.8 g) was dissolved in toluene and added dropwise to a stirred mixture of N-chloroacetyl-2-ethyl-6-methylaniline (21.2 g), polyethyleneglycol-400 (8.0 g), sodium hydroxide (16.0 g in 15 ml water) and toluene at such a rate to maintain the reaction temperature at 10°–15° C. for 2 hours.

The resulting white suspension was diluted with water and stirred for a further 15 minutes. The aqueous layer was separated. The organic layer was washed with water to pH 7, dried over magnesium sulphate and evaporated to yield a red oil (29.8 g). The crude product was taken up in light petrol (b.p. 40–60) and the insoluble material was discarded. The solution was washed with water, dried and evaporated to yield acetochlor as an orange oil (20.4 g), NMR (CDCl$_3$); δH 1.2(m,6H), 2.28(s,3H), 2.57(m,2H), 3.75(m,4H), 5.05 (m,2H), 7.1–7.35(m,3H).

Note: This procedure is modified from the process described in Zupancic et al., Synthesis (1982), page 942.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What we claim is:

1. A method of controlling the growth of weeds at a locus which comprises applying to said locus a synergistic herbicidally effective amount of:

(a) a 4-benzoylisoxazole of formula I:

wherein

R is hydrogen or —CO$_2$R$^3$, where R$^3$ is as defined below;

R$^1$ is cyclopropyl;

R$^2$ is selected from the group consisting of halogen, —S(O)$_p$Me and trifluoromethyl;

n is two or three; p is zero, one or two; and R$^3$ is C$_{1-4}$ alkyl; and (b) a chloroacetamide herbicide.

2. The method according to claim 1 in which the chloroacetamide herbicide is of formula (II):

wherein R$^{21}$ represents hydrogen, C$_{1-6}$ alkyl, haloalkyl, alkoxy or alkoxyalkyl; alkenyl, haloalkenyl, alkynyl, haloalkynyl or acylamidoalkyl having up to six carbon atoms;

Ar represents thienyl or phenyl, optionally bearing one or more groups selected from the group consisting of halogen, amino, C$_{1-6}$ alkyl, haloalkyl, alkoxy and alkoxyalkyl.

3. The method according to claim 2 wherein R$^{21}$ is selected from the group consisting of methoxymethyl, ethoxymethyl, 2-methoxy-1-methylethyl and 1-methylethyl.

4. The method according to claim 2 wherein Ar represents phenyl or thienyl optionally substituted by one or two groups which may be the same or different selected from the group consisting of ethyl and methyl.

5. The method according to claim 2 wherein R$^{21}$ represents methoxymethyl and Ar represents 2,6-diethylphenyl, which is alachlor.

6. The method according to claim 2 wherein R$^{21}$ represents ethoxymethyl and Ar represents 2-ethyl-6-methylphenyl, which is acetochlor.

7. The method according to claim 2 wherein R$^{21}$ represents 2-methoxy-1-methylethyl and Ar represents 2-ethyl-6-methylphenyl, which is metolachlor.

8. The method according to claim 2 wherein R$^{21}$ represents 1-methylethyl and Ar represents phenyl, which is propachlor.

9. The method according to claim 2 wherein R$^{21}$ represents 2-methoxy-1-methylethyl and Ar represents 3-(2,4-dimethyl)thienyl, which is dimethenamid.

10. The method according to claim 1 wherein for the 4-benzoylisoxazole of formula (I), R$^2$ is selected from the group consisting of halogen, —S(O)$_p$Me and trifluoromethyl.

11. The method according to claim 1 wherein for the 4-benzoylisoxazole of formula (I) n is three and the groups (R$^2$)$_n$ occupy the 2, 3 and 4-positions of the benzoyl ring.

12. The method according to claim 1 wherein for the 4-benzoylisoxazole of formula (I) n is two and the groups $(R^2)_n$ occupy the 2 and 4- positions of the benzoyl ring.

13. The method according to claim 1 in which one of the groups $R^2$ is —$S(O)_p$Me, wherein p is as defined in claim 1.

14. The method according to claim 1 wherein R is hydrogen.

15. The method according to claim 1 wherein the 4-benzoylisoxazole of formula (I) is:

5-cyclopropyl-4-(2-methylsulfonyl-4-trifluoromethyl) benzoylisoxazole;

5-cyclopropyl-4-(4-methylsulfonyl)-2-trifluoromethyl) benzoylisoxazole;

4-(2-chloro-4-methylsulfonyl)benzoyl-5-cyclopropyl-isoxazole;

4-(4-chloro-2-methylsulfonyl)benzoyl-5-cyclopropylisoxazole; or 4-(4-bromo-2-methylsulfonyl)benzoyl-5-cyclopropylisoxazole.

16. The method according to claim 1 wherein the 4-benzoylisoxazole of formula (I) is 5-cyclopropyl-4-(2-methylsulfonyl-4-trifluoromethyl)benzoylisoxazole.

17. The method according to claim 1 using from 0.5 g to 512 g of the 4-benzoylisoxazole and from 8 to 4000 g of the chloroacetamide herbicide per hectare.

18. The method according to claim 16 using from 0.5 g to 512 g of the 4-benzoylisoxazole and from 20 to 4000 g of the chloroacetamide herbicide per hectare.

19. The method according to claim 16 using from 20 to 200 g of 4-benzoylisoxazole and from 200 to 3000 g of the chloroacetamide herbicide per hectare.

20. The method according to claim 16 using from 25 to 150 g of 4-benzoylisoxazole and from 350 to 2000 g of the chloroacetamide herbicide per hectare.

21. The method according to claim 1 by pre-emergence application.

22. The method according to claim 21 by pre-plant application.

23. The method according to claim 1 in which the locus is an area used, or to be used, for the growing of a crop.

24. The method according to claim 23 in which the crop is maize.

25. A synergistic herbicidal composition comprising:

(a) a 4-benzoylisoxazole of formula I:

(I)

wherein

R is hydrogen or —$CO_2R^3$, where $R^3$ is as defined below;

$R^1$ is cyclopropyl;

$R^2$ is selected from the group consisting of halogen, —$S(O)_p$Me and trifluoromethyl;

n is two or three; p is zero, one or two; and $R^3$ is $C_{1-4}$ alkyl; and (b) a chloroacetamide herbicide in association with a herbicidally acceptable diluent or carrier and/or surface active agent.

26. The composition according to claim 25 comprising from 0.05 to 90% by weight of a 4-benzoylisoxazole of formula (I) as defined in claim 25 and chloroacetamide herbicide.

27. The composition according to claim 25 in which the ratio of (a):(b) is from 1:8000 to 64:1 wt/wt.

28. The composition according to claim 25 in which the ratio of (a):(b) is from 1:150 to 1:1 wt/wt.

29. The composition according to claim 25 in which the ratio of (a):(b) is from 1:80 to 1:3 wt/wt.

30. The composition according to claim 25 in the form of a wettable powder or a water-dispersible granule.

31. The composition according to claim 25 in which the chloroacetamide herbicide is of formula (II):

Ar—$N(R^{21})COCH_2Cl$ (II)

wherein $R^{21}$ represents hydrogen, $C_{1-6}$ alkyl, haloalkyl, alkoxy or alkoxyalkyl; alkenyl, haloalkenyl, alkynyl, haloalkynyl or acylamidoalkyl having up to six carbon atoms;

Ar represents thienyl or phenyl, optionally bearing one or more groups selected from the group consisting of halogen, amino, $C_{1-6}$ alkyl, haloalkyl, alkoxy and alkoxyalkyl.

32. The composition according to claim 31, wherein $R^{21}$ represents a group selected from the group consisting of methoxymethyl, ethoxymethyl, 2-methoxy-1-methylethyl and 1-methylethyl.

33. The composition according to claim 31 wherein Ar represents phenyl or thienyl optionally substituted by one or two groups which may be the same or different selected from the group consisting of ethyl and methyl.

34. The composition according to claim 31 wherein $R^{21}$ represents methoxymethyl and Ar represents 2,6-diethylphenyl, which is alachlor.

35. The composition according to claim 31 wherein $R^{21}$ represents ethoxymethyl and Ar represents 2-ethyl-6-methylphenyl, which is acetochlor.

36. The composition according to claim 31 wherein $R^{21}$ represents 2-methoxy-1-methylethyl and Ar represents 2-ethyl-6-methylphenyl, which is metolachlor.

37. The composition according to claim 31 wherein $R^{21}$ represents 1-methylethyl and Ar represents phenyl, which is propachlor.

38. The composition according to claim 31 wherein $R^{21}$ represents 2-methoxy-1-methylethyl and Ar represents 3-(2,4-dimethyl)thienyl, which is dimethenamid.

39. The composition according to claim 25 wherein for the 4-benzoylisoxazole of formula (I) $R^2$ is selected from the group consisting of halogen, —$S(O)_p$Me and trifluoromethyl, where p is as defined in claim 25.

40. The composition according to claim 25 wherein for the 4-benzoylisoxazole of formula (I) n is three and the groups $(R^2)_n$ occupy the 2,3 and 4-positions of the benzoyl ring.

41. The composition according to claim 25 wherein for the 4-benzoylisoxazole of formula (I) n is two and the groups $(R^2)_n$ occupy the 2 and 4- positions of the benzoyl ring.

42. The composition according to claim 25 wherein one of the groups $R^2$ is —$S(O)_p$Me, where p is as defined in claim 25.

43. The composition according to claim 25 wherein the 4-benzoylisoxazole of formula (I) is:

5-cyclopropyl-4(2-methylsulfonyl-4-trifluoromethyl) benzoylisoxazole;

5-cyclopropyl-4-(4-methylsulfonyl-2-trifluoromethyl) benzoylisoxazole;

4-(2-chloro-4-methylsulfonyl)benzoyl-5-cyclopropylisoxazole;

4-(4-chloro-2-methylsulfonyl)benzoyl-5-cyclopropylisoxazole; or 4-(4-bromo-2-methylsulfonyl)benzoyl-5-cyclopropylisoxazole.

44. The composition according to claim 25 wherein the 4-benzoylisoxazole of formula (I) is 5-cyclopropyl-4-(2-methylsulfonyl-4-trifluoromethyl)benzoylisoxazole.

45. The composition according to claim 44 wherein the chloroacetamide herbicide is acetochlor, which is 2-chloro-N-ethoxymethyl-6'-ethylacet-o-toluidide.

46. The composition according to claim 44 wherein the chloroacetamide herbicide is metolachlor, which is 2-chloro-6'-ethyl-N-(2-methoxy-1-methylethyl)acet-o-toluidide.

47. The composition according to claim 44 wherein the chloroacetamide herbicide is dimethenamid, which is 2-chloro-N-(2,4-dimethyl-3-thienyl)-N-(2-methoxy-1-methylethyl)acetamide.

48. A product comprising a synergistic herbicidally effective amount of:

(a) a 4-benzoylisoxazole of formula I:

wherein
R is hydrogen or —$CO_2R^3$, where $R^3$ is as defined below;
$R^1$ is cyclopropyl;
$R^2$ is selected from the group consisting of halogen, —$S(O)_p$Me and trifluoromethyl;
n is two or three; p is zero, one or two; and $R^3$ is $C_{1-4}$ alkyl; and (b) a chloroacetamide herbicide;

as a combined preparation for simultaneous, separate or sequential use in controlling the growth of weeds at a locus.

49. The composition according to claim 25 in which the ratio of (a):(b) is from 1:80 to 1:23 wt/wt.

* * * * *